United States Patent [19]

Borch et al.

[11] Patent Number: 5,190,929
[45] Date of Patent: Mar. 2, 1993

[54] CYCLOPHOSPHAMIDE ANALOGS USEFUL AS ANTI-TUMOR AGENTS

[75] Inventors: Richard F. Borch, Pittsford, N.Y.; Gregory W. Canute, Ann Arbor, Mich.

[73] Assignee: Research Corporation Technologies, Inc., Tuscon, Ariz.

[21] Appl. No.: 198,406

[22] Filed: May 25, 1988

[51] Int. Cl.$^5$ .................. C07F 9/6584; A61K 31/675
[52] U.S. Cl. ........................ 514/80; 514/82; 514/85; 514/86; 514/89; 514/91; 514/92; 514/94; 514/95; 514/96; 514/99; 514/100; 514/110; 544/232; 546/22; 546/23; 548/112; 548/113; 548/413; 548/414; 549/6; 549/218; 549/220
[58] Field of Search .............. 558/81; 514/110, 80, 514/82, 86, 85, 89, 91, 92, 94, 95, 96, 99, 100; 544/232; 546/22, 23; 548/112, 113, 413, 414; 549/6, 218, 220

[56] References Cited

U.S. PATENT DOCUMENTS

3,808,297 4/1974 Takamizawa et al. ............ 558/81
4,623,742 11/1986 Schaeffler ........................ 558/81

OTHER PUBLICATIONS

Pazdur, Proc. Am. Soc. Clin. Oncology 3, p. 219 (1984).
Martin et al, Cancer Research 49, 2189 (1986).
Farmer, Chem-Biol. Interactions 18, 47-57 (1977).
Cox, I Adv. Mass Spectrum. Biochem & Medicine, 1, 59-71 (1976).
Cox II Biochem. Pharmacol 24 p. 599 (1975).
Shih, Heterocycles 24(6) 1599-603 (1986).
Cyclophosphamide, *Merck Index*, p. 2736.
Foster, *Journal of Pharmaceutical Sciences*, 67, 709-710 (1978).
Sakuri, Cancer Chemother. Cent., Japan Found. Cancer Res. 272-281 (1978).
Arndt, et al., *Cancer Research*, 47, 5932-5934 (1987).
Friedman, et al., *Cancer Treatment Reports*, 60, 337-345 (1976).
Carter, *Cancer Chemother Pharmacol*, 1, 15-24 (1978).
Camerman, et al., *J. Med. Chem.*, 26, 679-683 (1983).
Foster, et al., *J. Med. Chem.*, 24, 1399-1403 (1981).
Takamizawa, et al., *Journal of Medicinal Chemistry*, 21, 208-214 (1978).
White, et al., JACS, 101, 1937-1942 (1978).
Gurtoo, et al., *Journal of Biological Chemistry*, 256, 11691-11701 (1976).
Boyd, et al., *J. Med. Chem.*, 23, 372-375 (1980).
Ludeman, et al., *Drugs, Exp. Clin. Res.*, XII, 527-532 (1986).
Ludeman, et al., *J. Med. Chem.*, 29, 716-727 (1980).
Arnold, et al., *Arzneim, Forsch.*, 11, 143 (1961).
Shih, et al., *Heterocycles*, 9, 1277 (1978).
Shih, et al., *Heterocycles*, 24, 1599 (1986).
Shih, et al., *Heterocycles*, 22, 2799 (1984).
Ludeman et al, "J. Med. Chem.", vol. 22, No. 2, (1979), pp. 151-158.

*Primary Examiner*—Mark L. Berch
*Attorney, Agent, or Firm*—Scully, Scott, Murphy & Presser

[57] ABSTRACT

Cyclophosphamides possessing anti-tumor activity and having the formula

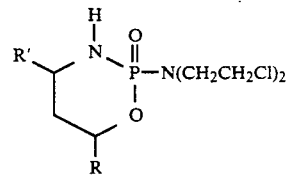

and salts thereof; wherein
R is lower alkyl, aryl, aryl-lower alkyl or a nitrogen, sulfur or oxygen containing heterocyclic or heterocyclic lower alkyl, and
R' is hydrogen, hydroxy or OOH with the proviso that when R' is hydrogen, R is other than methyl or phenyl and when R' is hydroxy, R is other than methyl.

27 Claims, No Drawings

CYCLOPHOSPHAMIDE ANALOGS USEFUL AS ANTI-TUMOR AGENTS

This invention relates to novel cyclophosphamides which have useful pharmaceutical properties and are useful as anti-tumor agents.

BACKGROUND OF THE INVENTION

Cyclophosphamide (also known as cytoxan) is one of the most widely used anti-cancer drugs in the world. It is administered in combination with a number of other drugs to treat a wide variety of hematologic and solid tumors. However, there are several features of the drug that can detract from its clinical efficacy. First, the drug requires metabolic activation in the liver to produce metabolites that are toxic to cancer cells. Second, the drug is specifically toxic to the urinary bladder and also displays the bone marrow toxicity typical of the alkylating agent class of anti-cancer drugs. Third, cyclophosphamide is a potent suppressor of the immune system at the doses used to treat cancer, thus decreasing the infection-fighting ability of patients already debilitated by their disease. Finally, repeated use of cyclophosphamide frequently results in the development of resistance to the drug in a patient's cancer cells, thus rendering the drug ineffective.

The present invention describes new cyclophosphamide compounds that will circumvent one or more of these problems. The compounds of the present invention are effective in treating tumors in animals that have developed resistance to cyclophosphamide itself. These compounds are free of the urinary bladder toxicity exhibited by cyclophosphamide. Finally, compounds included within the present invention do not require metabolism in the liver to acquire anti-tumor activity.

BRIEF DESCRIPTION OF THE INVENTION

This invention relates to new chemical cyclophosphamides possessing anti-tumor activity or capable of possessing anti-tumor activity upon activation thereof. The compounds of the present invention are:

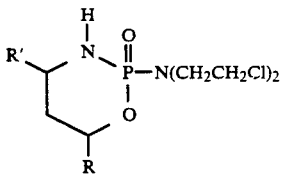

and pharmaceutically acceptable salts thereof wherein

R is lower alkyl, aryl, aryl-lower alkyl or a nitrogen, sulfur or oxygen containing heterocyclic or heterocyclic-lower alkyl and R' is hydrogen, hydroxy or hydroxperoxy with the proviso that when R' is hydrogen, R is not methyl or phenyl and with the further proviso that when R' is hydroxy, R is not methyl.

This invention also relates to pharmaceutical compositions containing as the active ingredient a compound of the formula:

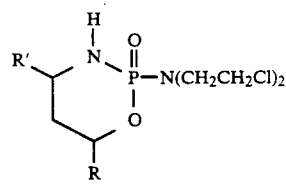

and pharmaceutically acceptable salts thereof wherein R' is hydrogen, hydroxy or hydroperoxy and R is a lower alkyl, aryl, aryl lower alkyl or a nitrogen, sulfur or oxygen containing heterocyclic or heterocyclic lower alkyl with the proviso that when R' is hydrogen, R is not methyl.

Finally, the present invention is directed to treating tumors which comprises administering to a host on anti-tumor effective amount of a compound of Formula II.

DETAILED DESCRIPTION OF THE INVENTION

In the foregoing description, the lower alkyl groups singly or in combination with other groups contain up to 6 carbon atoms which may be in the normal or branched configuration including methyl, ethyl, propyl, isopropyl, butyl, isobutyl, t-butyl, amyl, pentyl, hexyl and the like. The preferred alkyl groups contain one to three carbon atoms.

The aryl groups are aromatic rings containing from 6 to 10 ring carbon atoms. The aryl groups include phenyl, ∂-naphthyl and β-naphthyl. The aryl group is preferably phenyl.

The aralkyl· moieties are alkylene-aromatic groups which are bridged to the cyclophosphamide rings through the alkylene group, said alkylene group containing up to 6 carbon atoms. Such groups include benzyl, phenethyl, phenpropyl, ∂naphthylmethyl, and the like. The preferred arylalkyl group is phenethyl.

As employed herein, the expression "nitrogen, sulfur or oxygen heterocyclic ring" is meant to include those heterocyclic rings which include at least one sulfur, nitrogen or oxygen ring atom but which may include one or several of said atoms. The expression also includes saturated, and unsaturated heterocyclics as well as the heteroaromatic rings. These groups contain from 5 to 10 ring atoms on the heterocyclic moiety. Representative heterocyclics include furan, thiophene, pyrrole, pyridine, pyrazole, pyrazine, pyrimidine, pyridazine, oxazole, quinoline, isoquinoline, indole, benzothiophene, benzofuran, imidazole, benzoxazole, piperazine, tetrahydrofuran, and the like. The preferred heterocyclic is pyridyl, especially 3- or 4-pyridyl.

Heterocyclic lower alkyl groups are alkyleneheterocyclic groups bridged to the cyclophosphamide rings through the alkylene group, said alkylene group containing up to 6 carbon atoms. Such group includes pyridylethyl, pyrroly methyl, furylpropyl, tetrahydrofuryl-butyl, indolylmethyl, imidazolymethyl and the like.

Halo as defined herein is bromine, chlorine, or iodine and preferably fluorine.

The R groups may be unsubstituted or monosubstituted with a variety of substituents, such as lower alkyl, halo, lower alkoxy, nitro groups, nitrilo groups, formyl groups, carboxy groups, lower alkanoyl groups, carboxamido, amino, aminoalkyl, alkylamino, dialkylamino, hydroxy, alkyl thio, mercapto, and the like. It is preferred that said substituents be present on the intermediate compounds used in forming the final products. It is preferred that the alkyl groups, the aryl groups, e.g., phenyl, and the heterocyclic groups e.g., pyridyl be unsubstituted, or monosubstituted with nitro, halo or alkyl. Moreover, the preferred substitution on the phenyl group is on the para position. The preferred substituted phenyl groups are p-nitrophenyl, p-tolyl and p-fluorophenyl.

The preferred heterocyclic groups for R are 4-pyridyl and 2-,3-, or 4-nitroquinolyl.

As indicated hereinabove, R can also be heterocyclicalkyl. The preferred heterocyclic alkyl groups are imidazolyl-methyl. Moreover, it is especially preferred that the imidazolyl moiety be unsubstituted or monosubstituted with nitro. Preferred embodiments when R is heterocyclic alkyl are:

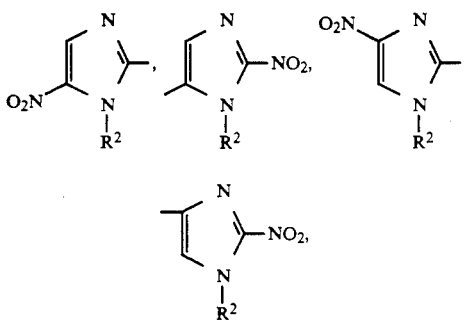

wherein $R^2$ is lower alkyl, which may be unsubstituted or substituted with OH or $NH_2$.

The compounds of the present invention can be prepared by art-recognized techniques. An examplary procedure is outlined hereinbelow in the following scheme:

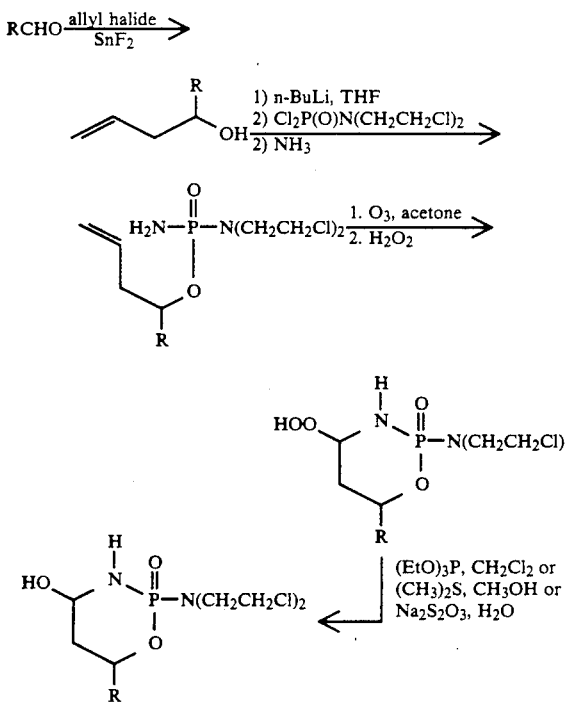

An aldehyde (RCHO) is reacted with an allylic halide, such as allyl iodide, in the presence of an acid such as a $SnF_2$. The resulting allyl alcohol is then reacted with a strong base, such as n-bulty-lithium in an inert solvent, e.g. hexanes, ethers (tetrapydrofuran) and the like. N,N-bis(2-chloroethyl) phosphoramidic dichloride is added to the basic solution followed by the addition of gaseous ammonia. The butenyl phosphoramidate resulting therefrom undergoes ozonolysis followed by subsequent treatment with hydrogen peroxide to give the 4-hydroperoxy derivative.

The 4-hydroperoxy compounds are intermediates in the synthesis of the 4-hydroxy compounds. The 4-hydroperoxy compounds are rapidly reduced in vitro or in vivo to the corresponding 4-hydroxy compounds by chemical as well as by enzymatic means. For example, the hydroperoxy can be reduced with triethyl phosphite in methylene chloride, with dimethyl sulfide in methanol and with sodium thiosulfate in water.

The reactions described hereinabove can be run at the temperatures effective for the desired transformation. This temperature ranges from the $-40°$ C. to reflux temperatures, but it is preferred that the reaction is run from $-10°$ C. to room temperature.

The present new compounds which contain basic nitrogen atoms can form salts with acids. All such acid salts are contemplated by the invention but especially preferred are salts with pharmaceutically acceptable acids, such as hydrochloric, sulfuric, nitric, toluenesulfonic, acetic, propionic, tartaric, malic and similar such acids well known in this art. In addition, quaternary salts can be formed using standard techniques of alkylation employing, for example, hydrocarbyl halides or sulfates such as methyl, ethyl, benzyl, propyl or allyl halides or sulfates.

The compounds of the present invention can be administered..to the host in a variety of forms adapted to the chosen route of administration, i.e., orally, intravenously, intramuscularly or subcutaneous routes.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains an amount ranging from about 100 mg to about 5 g of active compound. Preferred dosage ranges from about 10 to about 500 mg of active compound. Especially preferred dosage ranges from about 25 to 100 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavoring agent such as peppermint, oil of wintergreen, or cherry flavoring may be added. When the dosage unit form is a capsule, it may contain, in -addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially nontoxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of micro-organisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterilefiltered solution thereof.

The following examples further illustrate the invention.

EXAMPLE 1

4-Hydropenoxy-6-phenylcyclophosphamide

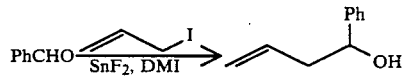

Preparation of 1-phenyl-3-buten-1-ol

A suspension of stannous fluoride (3.45 g, 0.022 mol) allyl iodide (3.36 g, 0.02 mol) and benzaldehyde (1.70 g, 0.016 mol) in 60 ml of 1,3-Dimethyl-2-imidazolidinone (DMI) was stirred for 1 hour at room temperature. Water was added to the reaction and the solution was extracted with ether (3×50 ml). The combined organic extracts were washed with brine (1×50 ml), dried over $MgSO_4$ and concentrated The resulting oil was subjected to flash chromatography with 1:5 EtOAc:hexanes as mobile phase to give pure product (2.69 g, 91%) $R_f$ 0.71 (EtOAc:hex 1:2) $^1$H NMR (CDCl$_3$) $\delta$7.35 (m, 5H), $\delta$5.80 (m, 1H),$\delta$5.16 (m, 2H) $\delta$4.73 (m, 1H), $\delta$2.51 (m, 2H) $\delta$2.06 (br s, 1H). IR (neat) 3400, 3070, 3025, 3000, 2975, 2930, 2905, 2870, 1725, 1640, 1600, 1490, 1450, 1430, 1370, 1305, 1245, 1195, 1110, 1070, 1040, 1025, 1000, 940, 915, 870, 845, 825, 760, 700, 640 cm$^{-1}$.

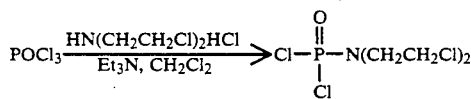

Preparation of Bis-(2-chloroethyl)phosphoramide dichloride

A solution us oxychloride (15.33 g, 0.10 mol) in CH$_2$Cl$_2$ (80 ml) was cooled to 0°. Bis-(2-chloroethyl)amine hydrochloride (17.85 g, 0.10 mol) was added directly. Triethylamine (30.66 ml, 0.22 mol) was added dropwise with constant stirring at 0° with a steady flow of nitrogen exiting through an aqueous solution of NaHCO$_3$. The reaction was then warmed to room temperature by allowing the ice bath to melt. After stirring for 34 hours, 10% KH$_2$PO$_4$ in water (60 ml) was added. The solution was extracted with CH$_2$Cl$_2$ (3×30 ml) and the combined organic extracts washed again with 10% aq. KH$_2$PO$_4$ (3×20 ml) then dried over MgSO$_4$. Removal of solvent under reduced pressure gave a crude solid which was distilled (d:p. 121°-122°, 0.5 mm) to provide pure product (19.3 g, 84%) as a white solid; $R_f = ^{31}$P NMR (CHCl$_3$)$\delta = -7.14$ ppm
IR (nujol) 1290, 1275, 1260, 1220 (P=O), 1195, 1160, 1150, 1110, 1095, 1060, 1030, 1010, 980, 975, 940, 920, 885, 850, 770, 750, 710, 665 cm$^{-1}$.

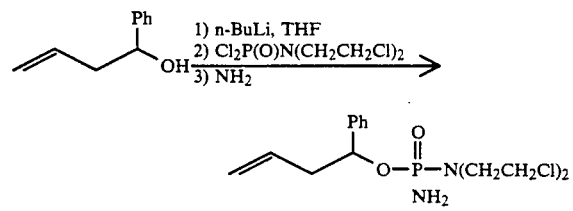

0-(1-phenyl-3-butenyl)-N,N-bis(2-chloroethyl) phosphorodiamidate

A solution of the butenyl alcohol prepared in A (2.0 mmol) in THF (10 ml) was treated dropwise with n-BuLi (1.48 ml. 1.1 eq) at room temperature. After 30 min, the solution was transferred via cannula to a 25 ml addition funnel. The alkoxide was then added dropwise at 0° to a flask which had first been charged with the cyclophosphamide (485 mg, 2.1 mmol) and THF (5.0 ml). The reaction was stirred at 0° for 30 min. after the addition was complete. Gaseous ammonia was bubbled through the mixture at 0° for 10 minutes and the resulting milky solution warmed to room temperature as the ice bath was allowed to melt. After stirring at room temperature for 2 hrs, the ammonium chloride was removed by filtration through celite and the solvents removed under reduced pressure.

A pale yellow oil (646 mg. 92%) was isolated. The compound could be used directly without further purification. Flash chromatography was used to prepare an analytical sample with 3:2 $CH_2Cl_2$: acetone as mobile phase which gave the product as a white solid (m.p. 65°–67°); $R_f$ 0.50 ($CH_2Cl_2$:acetone 2:1). Anal. Calcd. for $C_{14}H_{21}cl_2N_2O_2P$: C, 47.88; H, 6.03. Found: C, 47.75; H, 6.16. $^1H$ NMR ($CDCl_3$) 7.36 (m, 5H), δ5.71 (m, 1H), δ5.36 (d of t, $J_t$=6.0, $J_P$=8.2, 1H), δ5.11 (m, 2H), δ3.37 (m, 4H), δ3.12 (m, 4H), δ2.68 (br s, 2H, 2.65 (m, 2H). $^{31}P$ NMR ($CHCl_3$) δ-9.77; (acetone) δ-8.05,δ-8.15.

IR (nujuol) 3360, 3260, 3250, 3140, 1660, 1550, 1305, 1290, 1250, 1210, 1150, 1130, 1080, 1015, 990, 960, 930, 920, 860, 840, 780, 755, 740, 720, 690, 630 cm$^{-1}$.

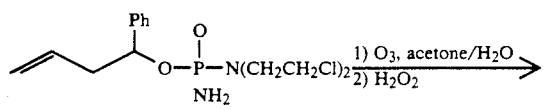

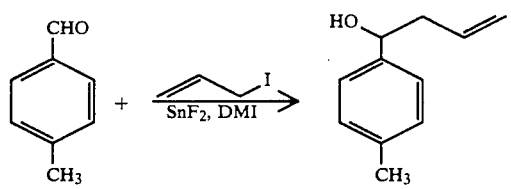

4-hydroperoxy-6-phenyl cyclophosphamide 3.0 g (8.56 mMol) of 1-phenyl-3-butenyl N,N-bis(2-chloroethyl) phosphorodiamidate was dissolved in 30 ml of 3:1 acetone: $H_2O$ and cooled to 0° C. After ozone was passed through the solution with stirring for 30 min., oxygen was passed through the solution for 2 min. to flush out excess ozone. Acetone was added to restore the initial reaction volume, 3 ml of 30% $H_2O_2$ was added, and the reaction was allowed to stir overnight at room temperature. The acetone was removed by evaporation in vacuo, the remaining two phase mixture extracted with $CHCl_3$ (3×20 ml), dried over $MgSO_4$, and evaporated in vacuo to an oil. Crystallization from $CH_2Cl/Et_2O$/pet. ether yielded 950 mg (30%) of diastereomerically pure product in which the hydroperoxy and phosphoryl oxygen groups were cis with respect to each other and trans to the 6-phenyl substituent. The filterate was evaporated under pressure and crystallized from $CH_2Cl_2/Et_2O$ to yield an additional 888 mg (28%, 58% overall) of product as a mixture of isomers. This mixture could be purified by flash chromatography (3:7 acetone: $CH_2Cl_2$, isomer 1, $R_f$=0.65, isomer 2, $R_f$=0.40) to provide a pure sample of the isomer in which the phosphoryl oxygen and phenyl groups were cis with respect to each other trans to hydroperoxy substituent.

EXAMPLE 2

Preparation of 4-hydroxy-6-phenylcyclophosphamide.

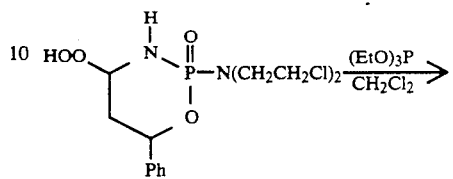

A solution of 4-hydroperoxy-6-phenylcyclophosphamide (100 mg, 0.3 mmol) was dissolved in 3 ml of methylene chloride and placed in a 20° water bath. Triethyl phosphite (70 ul, 0.4 mmol) was added to the stirred solution. After stirring for an additional 10 minutes, the solvent and excess reagent were removed under reduced pressure to give 95 mg (95%) of product that was pure by NMR, HPLC, and TLC.

EXAMPLE 3

4-Hydroperoxy-6-p-tolylcyclophosphamide

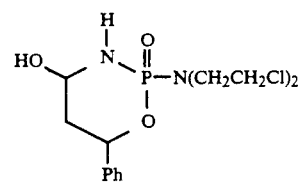

A. Preparation of 1-(p-tolyl)-3-buten-1-ol 5.90 ml (50 mmol) p-tolualdehyde was dissolved in 150 ml of DMI, and 5.5 ml (60 mmol, 1.2 eq.) allyl iodide and 10.34 g (66 mmol, 1.3 eq.) $SnF_2$ were added. The reaction became warm to the touch and much precipitate formed as the reaction progressed. After stirring for 1 hour at room temperature, 200 ml of $H_2O$ was added, the mixture was extracted with $Et_2O$ (1×250 ml, 2 ×100 ml), the combined $Et_2O$ layers were washed with sat. $NH_4Cl$ (3×50 ml, to remove excess DMI), dried over $MgSO_4$, and evaporated in vacuo to an oil. Flash chromatography (1:4 EtOAc:hexanes, $R_f$ 0.56) yielded 7.5 g (93%) of product as a clear oil. $^1H$ NMR ($CDCl_3$): 7.25 and 7.15 (4H, phenyl), 5.8 and 5.15 (3H, vinyl), 4.65 (1H, CHOH), 2.5 (2H, $CH_2$), 2.35 (2H, $CH_2$), 2.35 (3H, $CH_3$), and 2.15 (1H, OH) ppm.

B. Preparation of 1-(p-toly)-3-butenyl N,N-bis (2-chloroethyl)phosphorodiamidate

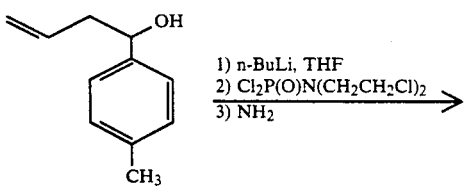

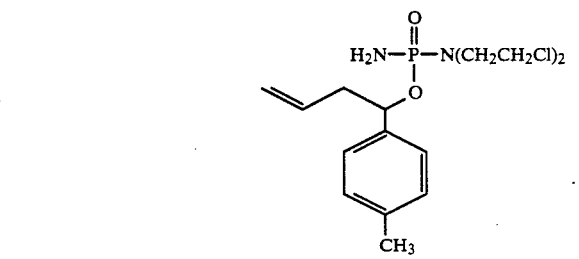

6.1 g (37.6 mmol) of 1-(p-tolyl)-3-buten-1-ol and a trace quantity of phenylazodiphenylamine indicator were dissolved in 100 ml THF and cooled to 0° C. A solution of 1.6 M n-BuLi in hexanes was added dropwise with stirring until the indicator turned purple. N,N-bis(2-chloroethyl) phosphoramidic dichloride, (9.74 g, 37.6 mmol) prepared as described in Example 1B was added to the cold stirred alkoxide solution in one portion, and the solution stirred for an additional 20 min. at 0° C. Gaseous $NH_3$ was bubbled through the solution at 0° C. for 15 min. The resulting suspension was briefly evaporated in vacuo to remove excess $NH_3$ and filtered through a pad of Celite. The pad was washed with ethyl acetate and the filtrate evaporated under reduced pressure to give a yellow oil. Flash chromatography (1:4 acetone: $CH_2Cl_2$, $R_f=0.59$) yielded 12.34 g (90%) of product as a yellow oil. An analytical sample was prepared by crystallization from ether/hexane: mp 58°–62°. Anal. calcd. for $C_{15}H_{23}N_2O_2Cl_2P$: C, 49.33; H, 6.35; found: C,48.89; H, 6.36.

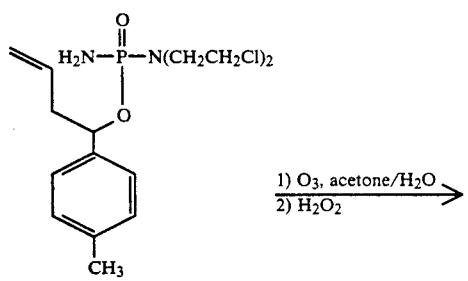

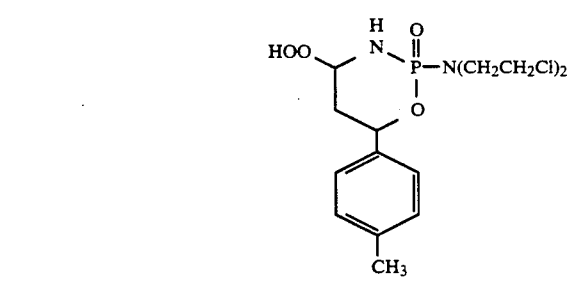

C. Preparation of 4-hydroperoxy-6-(p-tolyl) cyclophosphamide 1-p-tolyl-3-butenyl N,N-bis(2-chloroethyl)phosphorodiamidate 18.56 mMol) is dissolved in 30 ml of 3:1 acetone: $H_2O$ and cooled to 0° C. After ozone is passed through the solution with stirring for 30 min., oxygen is passed through the solution for 2 min. to flush out excess ozone. Acetone is added to restore the initial reaction volume, 3 ml of 30% $H_2O_2$ is added, and the reaction is allowed to stir overnight at room temperature. The acetone is removed by evaporation in vacuo, the remaining two phase mixture is extracted with $CHCl_3$ (3×20 ml), dried over $MgSO_4$, and evaporated in vacuo to an oil. Crystallization from $CH_2Cl_2/Et_2O$/pet. ether yields diastereomerically pure product in which the hydroperoxy and phosphoryl oxygen groups are cis with respect to each other and trans to the 6-phenyl substituent. The filtrate is evaporated under pressure and crystallized from $CH_2Cl_2/Et_2O$ to yield additional product as a mixture of isomers. This mixture is purified by flash chromatography (3:7 acetone: $CH_2Cl_2$), to provide a pure sample in which the phosphoryl oxygen and phenyl groups were cis with respect to each other and trans to the hydroperoxy substituent.

EXAMPLE 4

Preparation of 4-hydroxy-6-(p-tolyl)cyclophosphamide.

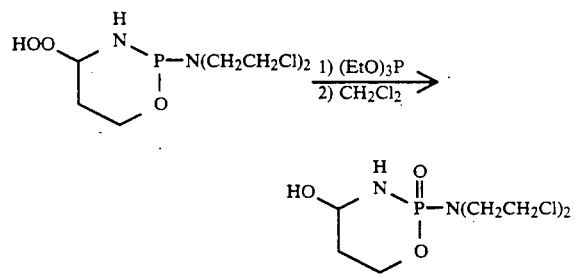

A solution of 4-hydroperoxy-6-(p-tolyl) cyclophosphamide (0.3 mMol) prepared in Example 1C was dissolved in 3 ml of methylene chloride and placed in a 20° water bath. Triethyl phosphite (70 ul. 0.4 mmol) is added to the stirred solution. After stirring for an additional 10 minutes, the solvent and excess reagent are removed under reduced pressure to obtain a product that is pure by NMR, HPLC, and TLC.

EXAMPLE 5

4-Hydroperoxy-6-(4-pyridyl)cyclophosphamide

A. Preparation of 1-(4-pyridyl)-3-buten-1-ol 4.75 g (50 mmol) of pyridine-4-carboxaldehyde was dissolved in 50 ml THF and cooled to 0° C. Allyl lithium was then added with stirring until the mixture turned the dark color characteristic of the allyl lithium solution. After stirring for an additional 5 minutes, water was slowly added at 0° C. until two phases formed and all precipitate was dissolved. The THF layer was separated, dried over $MgSO_4$, and evaporated in vacuo to an oil. Flash chromatography yielded 4.69 g (63%) of product as an oil. $^1$H NMR (CDCL$_3$): 8.5 and 7.3 (4H, pyridyl), 5.8 and 5.15 (3H, vinyl), 4.75 (1H, CHOH), 3.6 (1H, OH), and 2.5 (2H, $\underline{CH_2}$) ppm.

B. 4-hydroperoxy-6-(4-pyridyl)cyclophosphamide

Following the procedure of Example 1C and 1D, the above identified compound is prepared.

EXAMPLE 6

4-hydroxy-6-(4-pyridyl)cyclophosphamide

The above-identified product is prepared from 4-hydroperoxy-6-(4-pyridyl)cyclophosphamide in accordance with the procedure of Example 2.

EXAMPLE 7

Similarly, using the appropriate starting materials, the following compounds can be prepared in accordance with the procedures described herein:

4-hydroperoxy-6-methylcyclophosphamide
4-hydroxy-6-methylcyclophosphamide
4-hydroperoxy-6-isopropylcyclophosphamide
4-hydroxy-6-isopropylcyclophosphamide
4-hydroperoxy-6-phenethylcyclophosphamide
4-hydroxy-6-phenethylcyclophosphamide
4-hydroperoxy-6-p-nitrophenylcyclophosphamide
4-hydroxy-6-p-nitrophenylcyclophosphamide
4-hydroperoxy-6-p-fluorophenylcyclophosphamide
4-hydroxy-6-p-fluorophenyl cyclophosphamide
4-hydroxyperoxy-6-(3-pyridyl)cyclophosphamide
4-hydroxy-6-(3-pyridyl)cyclophosphamide The compounds of the present invention are effective anti-tumor agents and do not possess the disadvantage concomitant with the use of cyclophosphamide.

Cyclophosphamide (1) is a prodrug; i.e. it requires activation in the liver to be effective. More specifically, a hepatic mixed function oxidase converts the cyclophosphamide to 4-hydroxycyclophosphamide of unknown chemistry (2/3), which in turn forms an open chain aldophosphamide (4), as shown below. It is believed that the aldophosphamide undergoes B elmination in vivo to produce the active form, phosphoramide mustard, 6 (PDA). However, a side product of the process is acrolein. It is known that acrolein is the metabolite responsible for cyclophosphoramide bladder toxicity known as hemorrhagic cystitis.

These reactions are summarized below in Scheme II:

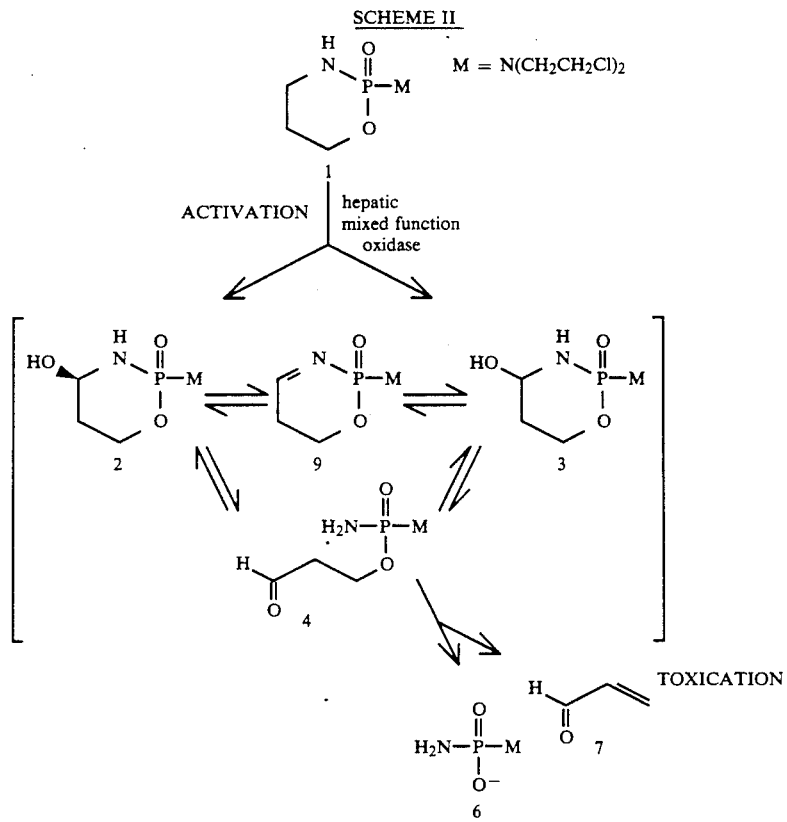

Addition of substituents at the 6-position of the cyclophosphamides of the present invention results in the production of a non-toxic metabolite rather than acrolein. This solves the problem of bladder toxicity.

The development of resistance to cyclophosphamide in several tumor lines has been shown to occur by enzyme inactivation of the aldophosphamide intermediate metabolite. Exposure of these tumor cells to cyclophosphamide results in the induction of the aldehyde dehydrogenase enzyme; this enzyme oxidizes the aldophosphamide to an inactive product. The substitution of a large group at the 6-position alters the equilibrium between the open (aldophosphamide) and cyclic intermediates so that the decreased fraction of open aldehyde intermediate would reduce its availability to the inactivating enzyme. NMR studies have confirmed that there is almost no detectable aldehyde intermediate present in these compounds.

Both the 4-hydroperoxy as well as the 4-hydroxy compounds of the present invention are pre-activated and therefore do not require metabolic activation for its efficacy. These compounds are therefore unlike cyclophosphamide, which required metabolic activation in order to function.

The cyclophosphamide in which the 4-position is unsubstituted, i.e, bears hydrogen, is non-activated and requires oxidation in the liver for activation.

The antitumor screening results presented hereinbelow demonstrate these compounds are markedly more active than cyclophosphamide against drug-resistant cells.

The In Vitro Cytotoxic activity of representative compounds of the present invention were evaluated as follows:

A soft agar colony-forming assay according to the procedure of Chu and Fischer, Biochem. Pharmacol., 17, 753–767 (1968) was used and modified where necessary. Cultured mouse L1210 and P388 sensitive cells were purchased from EG&G Mason Research Institute, Tumor Bank, Worchester, Mass. Cultured cyclophosphamide resistant L1210 and P388 cells were obtained from Dr. Robert Struck of Southern Research Institute, Birmingham, Ala. Typically, the desired cells $(2-3 \times 10^6$ cells/ml) in exponential growth and suspended in 6.5 ml of Fischer's medium (Gibco Lab., Grand Island, N.Y.) were divided into six groups (1 control and 5 treated groups) containing an equal number of cells in 1 ml. These cells were then treated with varying doses of drug (solution of perhydrooxazine in media or 20% ethanol-water), diluted with media to give a total volume of 10 ml, and incubated for one hour at 37° C. The cells were washed three times with 3 ml of supplemented Fischer's medium (containing 10% horse serum) by centrifuge (800×g), removal of media by suction, and resuspension of the pellet in media (5 ml). A 1-ml portion was used to determine the cell count with a Coulter counter. From the remainder, a 5-ml suspension of cells was prepared at a density of $10^5$ cells/ml, and between $10^2$ and $10^5$ cells were placed on soft agar and incubated at 37° C. Colonies were counted after 10 days. The log of the surviving fraction was plotted vs. drug concentration and from this plot the $LC_{99}$ was obtained. (By definition, the $LC_{99}$ value represents the concentration of drug necessary to effect a 99% cell kill.)

The results of the cytotoxic activity studies are tabulated hereinbelow:

TABLE 1

In Vitro Cytotoxic Evaluation of New Compounds Against Cyclophosphamide-sensitive (/0) and -resistant (/CP) L1210 and P388 Murine Leukemia Cells.

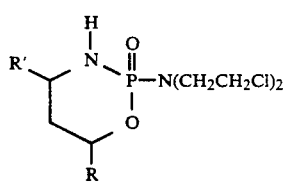

$LC_{99}$ Value (uM)

| Com- | | | L1210 | | | P388 | | |
|---|---|---|---|---|---|---|---|---|
| pound | R | R' | /0 | /CP | RF$^a$ | /0 | /CP | RF$^a$ |
| Ref | H | OOH | 8 | 141 | 17 | 6 | 60 | 10 |
| 1) | CH$_3$ | OOH | 32 | 177 | 5.5 | 26 | 69 | 2.7 |
| 2) | CH(CH$_3$)$_2$ | OOH | 105 | 115 | 1.1 | 86 | 61 | 0.7 |
| 3) | CH$_2$CH$_2$Ph | OOH | 11 | 9 | 1.1 | 9 | 5 | 0.6 |
| 4) | PH | OOH | 17 | 15 | 0.9 | 11 | 7 | 0.6 |
| 5) | p-NO$_2$Ph | OOH | 8 | 8 | 1.0 | 7 | 3 | 0.4 |
| 6) | p-CH$_3$Ph | OOH | 5 | 6 | 1.2 | 3 | 3 | 1.0 |
| 7) | p-FPh | OOH | 7 | 8 | 1.1 | 6 | 3 | 0.5 |
| 8) | 3-pyridyl | OOH | 36 | 56 | 1.6 | 33 | 24 | 0.7 |
| 9) | 4-pyridyl | OOH | 53 | 57 | 1.1 | 44 | 27 | 0.6 |

$^a$resistance factor RF = ratio of $LC_{99}$ in resistant/sensitive cells.

The data in Table 1 show substantial variation of antitumor activity depending upon the nature of the substituent (R) at the 6-position of the cyclophosphamide ring. Because the data reports the minimum concentration of drug needed to destroy 99% of the clonogenic cells after a 1-hour exposure, greater potency is represented by a smaller $LC_{99}$ value. The second point to note is that many of the compounds are essentially equitoxic to both cyclophosphamide-sensitive and cyclophosphamide-resistant cells, in contrast to the reference activated cyclophosphamide. This is apparent from the number of new analogs that have resistance factors of approximately unity, again in marked contrast to the 10- or 17-fold higher dose of activated cyclophosphamide required to kill the resistant cells.

In Vivo Antitumor Activity:

Typically 4 groups of 10 male B$_6$D$_2$F$_1$ mice (Jackson Breeding Lab., Bar Harbor Me) were injected i.p. with $1 \times 10^5$ L1210 tumor cells. Twenty four hours after injection three groups were treated (i.p. injection) with varying doses of drug, and the fourth group received the vehicle alone. The mice were observed daily and death dates were recorded. The experiment was terminated on day 30 and median survival time (days) and % T/C (ratio of median survival time of treated group divided by the mean survival time of the control group) was calculated. The drug was delivered using either an isotonic saline solution or a carboxymethyl cellulose suspension depending on the solubility of the drug.

TABLE 2

SURVIVAL OF L1210 BEARING MICE - % T/C × 100
(Long Term Survivors)

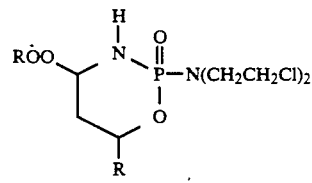

| | | Drug Dose (umol/kg) | | | |
|---|---|---|---|---|---|
| Compound | R | 17 | 34 | 51 | 68 |
| Ref | H | 136 | 194 | 50 | |
| 1. | Me | | 138 (2/6) | 56 | 50 |
| 2. | CH$_2$CH$_2$Ph | | 106 | 25 | |
| 3. | Ph | 117 | 144 | toxic | |
| 4. | p-NO$_2$Ph | | 163 (1/6) | 194 (2/6) | 225 (4/6) |
| 5. | p-tolyl | | 150 | 175 (1/6) | 180 (1/6) |
| 6. | p-FPh | | 163 | 188 (1/6) | 63 (1/6) |
| 7. | 3-pyridyl | | 131 | 69 | 63 |
| 8. | 4-pyridyl | 131 | 150 | 164 | 193 (1/6) |
| | | CP-resistant L1210 cells | | | |
| Ref | H | 112 | 100 | 75 | |
| 9. | 4-pyridyl | 119 | 131 | 138 | 150 |

The values reported in this table represent the percent increase in the survival time of L1210 Leukemic mice treated with each drug compared with the survival time of untreated leukemic mice. A value of 100% generally indicates that the survival time was shortened as a result of drug toxicity. A value of 125% is defined by the National Cancer Institute as the minimum value required to demonstrate antitumor activity; a value 150% is considered to represent substantial activity. The p-nitrophenyl compound 5, the p-tolyl compound 6, and the 4-pyridyl compound 9 are highly active at all doses tested and are less toxic at higher doses than the reference activated cyclophosphamide. The p-fluorophenyl analog 7 is highly active at the lower doses tested. When mice bearing the cyclophosphamide resistant L1210 leukemia are treated with activated cyclophosphamide, no significant increase in lifespan is observed, and toxicity is apparent at the 51 umol/kg dose. However, the 4-pyridyl analog 9 prolongs the survival of these mice bearing the drug-resistant leukemia at all doses tested.

The above preferred embodiments and examples are given to illustrate the scope and spirit of the present invention. These embodiments and examples will make apparent to those skilled in the art other embodiments and examples. These other embodiments are examples within the contemplation of the present invention. Therefore the present invention should be limited only by the appended claims.

What is claimed is:

1. A compound having the formula:

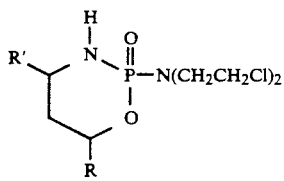

and pharmaceutically acceptable salts thereof wherein
R' is hydrogen, hydroxy or hydroperoxy, with the proviso that when R' is hydrogen, R is not phenyl;
R is unsubstituted or mono- or di-substituted aryl, wherein the substitutents are lower alkyl, halo, lower alkoxy, nitro, nitrilo, formyl, carboxy, lower alkanoyl, carboamido, amino, lower aminoalkyl, lower alkylamino, lower dialkylamino, hydroxy, lower alkylthio or mercapto.

2. A compound having the formula:

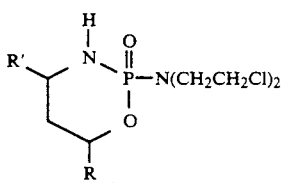

and pharmaceutically acceptable salts thereof wherein
R' is hydrogen, hydroxy or OOH,
R is aryl-lower alkyl which is unsubstituted or mono-substituted or disubstituted with lower alkyl, halo, lower alkoxy, nitro, nitrilo, formyl, carboxy, lower alkanoyl, carboamido, amino, lower aminoalkyl, lower alkylamino, lower dialkylamino, hydroxy, lower alkylthio or mercapto.

3. A compound having the formula:

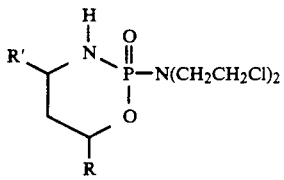

and pharmaceutically acceptable salts thereof wherein
R is an unsubstituted or mono- or di-substituted nitrogen, sulfur or oxygen containing heterocyclic wherein the substitutents are lower alkyl, halo, lower alkoxy, nitro, nitrilo, formyl, carboxy, lower alkanoyl, carboamido, amino, lower aminoalkyl, lower alkylamino, lower dialkylamino, hydroxy, lower alkythlthio or mercapto and
R' is hydrogen, hydroxy or OOH,
wherein heterocyclic is furyl, thienyl, pyrrolyl, pyridyl, pyrazolyl, pyrimidinyl, pyridazinyl, oxazolyl, quinolinyl, isoquinolinyl, indolyl, benzothienyl, benzofuryl, imidazoyl, benzoxazolyl, piperazinyl, or tetrahydrofuryl.

4. A compound having the formula:

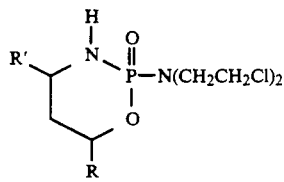

and pharmaceutically acceptable salts thereof wherein
R is nitrogen, sulfur or oxygen containing heterocyclic lower alkyl which is unsubstituted or mono-substituted or disubstituted, wherein the substitutents are lower alkyl, halo, lower alkoxy, nitro, nitrilo, formyl, carboxy, lower alkanoyl, carboamido, amino, lower amino alkyl, lower alkylamino, lower dialkylamino, hydroxy, lower alkylthio or mercapto, and
R' is hydrogen, hydroxy or OOH,
wherein heterocyclic is furyl, thienyl, pyrrolyl, pyridyl, pyrazolyl, pyrimidinyl, pyridazinyl, oxazolyl, quinolinyl, isoquinolinyl, indolyl, benzothienyl, benzofuryl, imidazoyl, benzoxazolyl, piperazinyl or tetrahydrofuryl.

5. The compound according to claim 1 wherein R is unsubstituted or mono- or disubstituted phenyl.

6. The compound according to claim 5, wherein R is mono substituted phenyl and the substituent is in the para position of the phenyl ring.

7. The compound according to claim 1, wherein R is phenyl which is unsubstituted or monosubstituted with nitro, halo or alkyl.

8. The compound according to claim 1 wherein R is p-nitrophenyl, p-tolyl or p-fluorophenyl.

9. A compound having the formula:

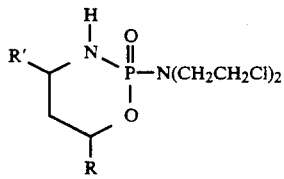

and pharmaceutically acceptable salts thereof wherein R is

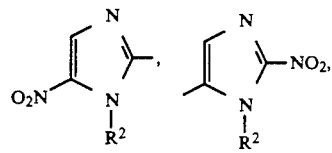

-continued

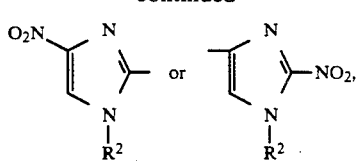

wherein R² is lower alkyl which is unsubstituted or monosubstituted with hydroxy or amino and wherein R' is hydrogen, hydroxy, or OOH.

10. The compound according to claim 2 wherein aryl-lower alkyl is benzyl, phenethyl, phenpropyl or α-naphthylmethyl.

11. The compound according to claim 2 wherein aryl-lower alkyl is phenethyl.

12. The compound is according to claim 3 wherein R is unsubstituted or monosubstituted with nitro, halo or lower alkyl.

13. The compound according to claim 12 wherein R is pyridyl.

14. The compound according to claim 3 wherein R is 3- or 4-pyridyl.

15. The compound according to claim 3 wherein R is 4-pyridyl or 2-, 3- or 4-nitroquinolyl.

16. The compound according to claim 4 wherein R is unsubstituted imidazolyl methyl or monosubstituted imidazolyl methyl wherein the substituent is nitro.

17. The compound according to claim 1 wherein A' is OH or OOH.

18. The compound according to claim 2 wherein A' is OH or OOH.

19. The compound according to claim 3 wherein R' is OH or OOH.

20. The compound according to claim 4 wherein R' is OH or OOH.

21. The compound according to claim 1 wherein R' is OOH and R is phenyl, p-nitrophenyl, p-tolyl, or p-fluorophenyl.

22. The compound according to claim 2 wherein R' is OOH and R is phenethyl.

23. The compound according to claim 3 wherein R' is OOH and R is 3-pyridyl or 4-pyridyl.

24. A pharmaceutical composition comprising a compound according to claim 1 and a pharmaceutical carrier therefor.

25. A pharmaceutical composition comprising a compound according to claim 2 and a pharmaceutical carrier therefor.

26. A pharmaceutical composition comprising a compound according to claim 3 and a pharmaceutical carrier therefor.

27. A pharmaceutical composition comprising a compound according to claim 4 and a pharmaceutical carrier therefor.

* * * * *

UNITED STATES PATENT AND TRADEMARK OFFICE
CERTIFICATE OF CORRECTION

PATENT NO. : 5,190,929

DATED : March 2, 1993

INVENTOR(S) : Richard F. Borch, et al.

Page 1 of 2

It is certified that error appears in the above-identified patent and that said Letters Patent is hereby corrected as shown below:

Column 1, line 1: insert --This invention was made with Government support under ROC-CA-34620 awarded by the National Institutes of Health. The Government has certain rights in the invention.--

Column 4, lines 36-37, after "administered" delete --..--

Column 5, line 4: "-addition" should read --addition--

Column 6, line 38: "us" should read --of--

Column 7, line 34: "$O_3$," should read --$O_3$'--

Column 9, line 6: "$NH_2$" should read --$NH_3$--

UNITED STATES PATENT AND TRADEMARK OFFICE
CERTIFICATE OF CORRECTION

PATENT NO. : 5,190,929
DATED : March 2, 1993
INVENTOR(S) : Richard F. Borch, et al.

It is certified that error appears in the above-identified patent and that said Letters Patent is hereby corrected as shown below:

Column 9, line 47: "$O_3$," should read --$O_3'$--
Column 10, line 65: "CH" should read --C$\underline{H}$--
Column 14, line 34: "ROO" should read --HOO--
Column 18, line 4, Claim 17: "A'" should read --R'--

Column 18, line 6, Claim 18: "A'" should read --R'--

Signed and Sealed this

First Day of February, 1994

Attest:

BRUCE LEHMAN

Attesting Officer    Commissioner of Patents and Trademarks